United States Patent

Kruse-Mueller et al.

Patent Number: 6,066,455
Date of Patent: May 23, 2000

[54] METHOD OF DETECTING NUCLEIC ACIDS

[75] Inventors: Cornelia Kruse-Mueller, Tutzing; Stefanie Koehler, Starnberg, both of Germany

[73] Assignee: Roche Diagnostics GmbH, Mannheim, Germany

[21] Appl. No.: 08/971,961

[22] Filed: Nov. 17, 1997

Related U.S. Application Data

[63] Continuation of application No. 08/466,722, Jun. 6, 1995, abandoned, which is a continuation of application No. 08/342,497, Oct. 18, 1994, abandoned, which is a continuation of application No. 08/046,858, Apr. 15, 1993, abandoned.

[30] Foreign Application Priority Data

Apr. 15, 1992 [DE] Germany .............................. 42 12 555

[51] Int. Cl.$^7$ ..................................................... C12Q 1/68
[52] U.S. Cl. ........................... 435/6; 435/91.1; 536/24.3; 536/24.33; 536/23.1; 935/1; 935/16; 935/77; 935/76

[56] References Cited

U.S. PATENT DOCUMENTS

| | | | |
|---|---|---|---|
| 4,652,517 | 3/1987 | Scholl et al. ................................. | 435/5 |
| 5,225,326 | 7/1993 | Bresser et al. ............................... | 435/6 |
| 5,231,015 | 7/1993 | Cummins et al. ........................ | 435/91 |
| 5,232,829 | 8/1993 | Longiaru et al. ............................ | 435/6 |

FOREIGN PATENT DOCUMENTS

| | | | |
|---|---|---|---|
| 0 079 139 | 5/1983 | European Pat. Off. . | |
| 0 132 948 | 2/1985 | European Pat. Off. . | |
| 0 200 362 B1 | 12/1986 | European Pat. Off. . | |
| O 281 927 | 3/1987 | European Pat. Off. . | |
| 0 235 726 | 9/1987 | European Pat. Off. . | |
| 0 258 017 | 3/1988 | European Pat. Off. . | |
| 0 261 955 | 3/1988 | European Pat. Off. . | |
| 0 261 955 A2 | 3/1988 | European Pat. Off. .......... | C12Q 1/68 |
| O 261 955 | 3/1988 | European Pat. Off. . | |
| 0 281 927 A3 | 9/1988 | European Pat. Off. .......... | C12Q 1/68 |
| O-428 197 | 10/1989 | European Pat. Off. . | |
| 0 428 197 A2 | 5/1991 | European Pat. Off. .......... | C12Q 1/68 |
| 0 471 293 A2 | 2/1992 | European Pat. Off. . | |
| WO 89/05357 | 6/1989 | WIPO . | |

OTHER PUBLICATIONS

Sommer and Tautz, *Nucleic Acids Research*, vol. 12, No. 16, 1989, p. 6749.

Seelig et al., "nachweis von Hepatitis–B–Virus–DNA mit der Polymerase–Kettenreaktion", DMW, vol. 115, pp. 1307–130, 1190.

Blum, et al., "Naturally Occurring Missense Mutation in the Polymerase Gene Terminating Hepatitis B Virus Replication", Journal of Virology, vol. 65, No. 4, p. 1836, Apr. 1991.

Holmes et al., "Harvesting and Lysis of Bacteria", Large–Scale Isolation of Plasmid DNA, pp. 89–91, 1981.

Tran et al., "Emergency of and Takeover by Hepatitis B Virus (HBV) with Rearrangements in the Pre–S/S and Pre–C/C Genes during Chronic HBV Infection", Journal of Virology, vol. 65, pp. 3566, 3568, Jul. 1991.

Kaneko et al., "Detection of Hepatitis B Virus DNA in Serum by Polymerase Chain Reaction", Gastroenterology, vol. 99, No. 3, pp. 799–800, 1990.

(List continued on next page.)

*Primary Examiner*—Kenneth R. Horlick
*Assistant Examiner*—Janell E. Taylor
*Attorney, Agent, or Firm*—Nikaido Marmelstein Murray & Oram, LLP

[57] ABSTRACT

Method of detecting a nucleic acid by converting the nucleic acid into a single-stranded nucleic acid under alkaline conditions, wherein at least one detergent from the group of anionic, non-ionic and zwitterionic detergents is present, adding an immobilizable or immobilized capture probe, hybridizing the capture probe with the nucleic acid under immobilization of the nucleic acid via the capture probe and detecting the amount of synthesized, immobilized hybrid.

15 Claims, 2 Drawing Sheets

OTHER PUBLICATIONS

Brunetto et al., "Wild–type and e antigen–minus hepatitus B viruses and course of chronic hepatitis", Prod. Ntal. Acad. Sci. USA, vol. 88, pp. 4186–4187, 1991.

Kaneko et al., "Rapid and Sensitive Method for the Detection of Serum Hepatitis B Virus DNA Using the Polymerase Chain Reaction Technique", Journal of Clinical Microbiology, vol. 27, p. 1930, Sep. 1989.

Ulrich et al., "Enzymatic Amplification of Hepatitis B Virus DNA . . . ", The Journal of Infectious Diseases, vol. 160, No. 1, pp. 37–38, Jul., 1989.

Keller et al., "Detection of Hepatitis B Virus DNA in Serum by Polymerase Chain Reaction Amplification and Microtiter Sandwich Hybridization", Journal of Clinical Microbiology, vol. 28, No. 6, p. 1416, Jun., 1990.

Lin et al., "An oligonucleotide probe for the detection of hepatitis B virus DNA in serum", Journal of Virological Methods, vol. 15, pp. 139–140, 1987.

Zyzik et al., "Assay of Hepatitis B Virus Genome Titers in Sera of Infected Subjects", Eur. J. Clin. Microbiol., vol. 5, No. 3, pp. 330–331, Jun., 1986.

METHOD OF DETECTING NUCLEIC ACIDS

This application is a continuation of application Ser. No. 08/466,722, filed on Jun. 6, 1995, now abandoned, which is a continuation of Ser. No. 08/342,497 filed on Oct. 18, 1994, abandoned, which is a continuation of Ser. No. 08/046,858 filed on Apr. 15, 1993, abandoned.

Subject matter of the invention is a method of detecting nucleic acids, the use of certain detergents for stabilizing single-stranded nucleic acids as well as a reagent kit and an analysis system for implementing said method.

In the field of nucleic acid hybridization tests, considerable progress has been made over the last decade with respect to utilizing the specific hybridization of two complementary nucleic acids. It is, for example, now possible to detect many parameters, e.g. infection parameters, not only by means of immunological tests but also by means of nucleic acid hybridization tests. The possibility of specifically replicating nucleic acids in-vitro prior to their detection and, hence, also detect those nucleic acids which, are present in the samples in only minor quantities has been particularly beneficial to this goal.

Owing to their relatively high complexity, these nucleic tests have so far only been used in individual tests which require complicated manual processing, of the sample. A typical example of such a test is described in EP-A-0 200 362. In this process, the amplified nucleic acids are subject to separation by means of gel electrophoresis. Subsequently, the presence of the nucleic acids in the gel is made visible with the aid of specific, labelled nucleic acid probes. Such processes are practically useless for routine diagnostics in laboratories with a high sample throughput.

EP-A-0 261 955 describes a method of detecting bacteria. Said method comprises the lysis of cell walls (by means of proteinase K), alkaline treatment to denature the DNA and, subsequently, immobilization of a single-stranded nucleic acid by adding a chaotropic agent. Due to the complicated individual steps, particularly the direct immobilization of nucleic acid to be detected on a membrane, this method is not feasible in routine laboratories.

As regards the lysis of bacteria, Maniatis et al. (Molecular Cloning, Sambrook et al. (editors), Cold Spring Harbor 1989) described conditions which include SDS (sodium dodecyl sulfate) under alkaline conditions. In this publication, the detection of nucleic acids is also carried out after direct immobilization of the nucleic acid and hybridization with a detector probe on a membrane. The conditions are suitable for laboratories working in molecular biology but not for application in routine diagnostics.

To date, a buffer (e.g. TE: 10 mM TrisxHcl, pH 7.4. 1 mM EDTA) in a neutral or slightly acidic or alkaline solution has been used or the DNA has been stored in water or lyophilized or frozen at $-20°$ C. or it has been stored as ethanol precipitate at $-20°$ C.

Again, it is practically not possible to employ these conditions in routine analysis procedures where emphasis is placed on high throughput and easy handling.

In order to reduce non-specific binding to filters, the addition of foreign DNA (e.g. herring sperm DNA) has been proposed. The additives proposed to facilitate hybridization of nucleic acids include polyvinylpyrrolidone, bovine serum albumin, Ficoll® (copolymerisate of epichlorhydrin and saccharose) and SDS.

According to EP-A-0 132 948, SB-16 (3-(hexadecyldimethylammonium)1-propane-sulfonate) reduces the non-specific binding of the conjugate consisting of avidin and alkaline phosphatase to nitrocellulose filter plates.

Further, this publication describes the siliconization of glass and plastic vessels to stabilize small amounts of DNA or single-strand DNA.

EP-A-0 258 017 describes the stabilization of DNA polymerase from Thermos aquaticus by means of non-ionic detergents.

It was, hence, an object of the present invention to provide a method of detecting analyte nucleic acids which meet the requirements of routine diagnostics laboratories in a more appropriate way.

Subject matter of the invention is a method of detecting a nucleic acid accompanying the following steps:

conversion into a single-stranded nucleic acid under alkaline conditions addition of an immobilizable or immobilized capture probe hybridization of the capture probe with the nucleic acid under immobilization of a nucleic acid via the capture probe and detection of the quantity of synthesized immobilized hybrid with at least one detergent from the group of the anionic, non-ionic and zwitterionic detergents being present during treatment under alkaline conditions.

Another subject matter of the invention is the use of certain detergents to stabilize nucleic acids in alkaline solutions as well as a reagent kit and an analysis system for implementing said method.

The method of the invention is a special embodiment of what is known as a hybridization test. Its fundamentals are known to the expert in the field of nucleic acid diagnostics. Unless otherwise mentioned in the text, all experimental details are fully described in "Nucleic Acid Hybridization", B. D. Hames and S. J. Higgins (editors), IRL Press, 1986, e.g. in chapters I (Hybridization Strategy), 3 (Quantitative Analysis of Solution Hybridization) and 4 (Quantitative Filter Hybridization), Current Protocols in Molecular Biology, F. M. Ausubel et al. (editors), J. Wiley and Son, 1987, and Molecular Cloning, J. Sambrook et al. (editors), CSH, 1989. Known methods also include the preparation of labelled nucleoside triphosphates as has been described in EP-A-0 324 474; the chemical synthesis of modified and non-modified oligonucleotides; the cleavage of nucleic acids with the aid of restriction enzymes; the selection of hybridization conditions to obtain the specificity which depends upon the extent of the homology between the nucleic acids to be hybridized, their GC contents and their lengths as well as the formation of nucleic acids from nucleoside triphosphates with the aid of polymerases, and, if necessary, with the aid of so-called primers.

A labelling as understood in the present invention includes a directly or indirectly detectable group L. Directly detectable groups include, for example, radioactive ($^{32}P$), colored, fluorescent groups or metal atoms. Indirectly detectable groups include, for example, immunologically or enzymatically active compounds such as antibodies, antigens, haptens or enzymes or enzymatically active partial enzymes. They are detected in a subsequent reaction or reaction sequence. Particularly preferred are haptens since hapten-labelled nucleoside triphosphates generally serve particularly well as substrates of polymerases, and it is easy to subsequently carry out a reaction with a labelled antibody to the hapten or the haptenized nucleoside. Such nucleoside triphosphates include, for example, bromide nucleoside triphosphates or digoxigenin, digoxin or fluorescein-coupled nucleoside triphosphates (corresponding to U.S. patent application Ser. No. 07/415,307 filed Jan. 9, 1990, which issued as U.S. Pat. No. 5,344,757 on Sep. 6, 1994). EP-A-0 324 474 mentions steroids and their detection, which have proven to be particularly suitable. For their incorporation in nucleic acids, reference is herewith made to EP-A-0 324 474.

Nucleoside triphosphates (NTP) are ribo (rNTP)- or deoxyribonucleoside triphosphates (dNTP).

An analyte nucleic acid is understood to be a nucleic acid which is to be detected. Analyte nucleic acids, hence, include nucleic acids of any origin, for example, nucleic acids of a viroid, viral, bacterial or cellular origin. They may be present in solution, suspension, but also fixed to solid bodies or contained in cell-containing media, cell smears, fixed cells, tissue particles or fixed organisms. Nucleic acids are preferably, present in the solution.

Normally, the reaction sequence is started by preparing the analyte nucleic acid with the corresponding reagents. This may be promoted by changing the pH (alkaline), heat-repeating extreme temperature changes (freezing/thawing), changing the physiological growth conditions (osmotic pressure), effect of detergents, chaotropic salts or enzymes (e.g. proteases, lipases). These factors may occur either alone or in combination in order to release the nucleic acids. As the method of the invention is very sensitive and selective, it also allows the detection of small amounts of nucleic acids in the presence of other substances, for example proteins, cells, cell fragments, but also in the presence of nucleic acids which are not to be detected. Sample purification is no longer required provided the nucleic acids to be detected are available in a sufficient amount, so as to engage in a reaction with the reagents used.

A template nucleic acid is a nucleic acid to which an essentially complementary nucleic acid strand is newly synthesized. The template nucleic acid contains the sequence information necessary for transcription.

Denaturing nucleic acids means separating double-stranded nucleic acids into single-stranded nucleic acids. Principally, the expert can choose from a variety of possibilities, e.g. treatment with alkali hydroxide, thermal or chemical treatment.

Specific detection refers to a method by which certain nucleic acids are detected selectively and in the presence of other nucleic acids. It is, however, also possible to detect a group of nucleic acids with a partly identical or similar nucleotide sequence. The detection of double-stranded nucleic acids may comprise each of the two complementary strands.

A nucleic acid or nucleic acid sequence which is essentially complementary to another nucleic acid is understood to be a nucleic acid or a sequence which is capable of hybridizing with the corresponding nucleic acid whose nucleotide sequence, in the hybridizing segment, is either exactly complementary to the other nucleic acid or differs by only a few bases from the exactly complementary nucleic acid. Specificity depends on both the degree of complementarity and the hybridization conditions.

The aqueous phase used in the detection of nucleic acids is usually a liquid phase, which may contain dissolved organic or inorganic substances, e.g. buffer substances, excess reagent, nucleic acids which are not to be detected, proteins, and the like.

The nucleic acid to be detected may be the analyte nucleic acid itself. However, it may also be a nucleic acid obtained from the analyte-nucleic acid through pretreatment in the sample liquid. Known pretreatment procedures include in particular fragmentation, for example, by means of restriction enzymes, or cDNA synthesis from RNA. For the method of the invention to fully unfold its advantages, it has proven advantageous if the nucleic acid to be detected has a minimum length of 40 bp.

Preferably, the nucleic acids to be detected is the product of an upstream specific or non-specific, nucleic acid replication. Such nucleic acid amplification processes are, for example, known from EP-A-0 201 184, EP-A-0 237 362, EP-A-0 329 822, EP-A-0 320 308 or WO 88/10315. In these processes, the analyte-nucleic acid serves as a template nucleic acid for the synthesis of the nucleic acid which is ultimately to be detected.

However, the nucleic acid may also be obtained by cloning and in-vivo replication.

The method for detecting a special virus in a body fluid (e.g. serum) may start with the lysis of the virus envelope as a first step. The expert is familiar with methods of lysing cell walls. Lysis can, for example, be done by treatment with alkali hydroxide solutions. Another possibility is the addition of additives, for example, detergents. Especially in the case of viruses which are present in body fluids only at small concentrations (e.g. hepatitis C virus) this step may be followed by in-vitro replication of the nucleic acid (e.g. via polymerase chain reaction or one of the other above-mentioned amplification processes). Here, the analyte nucleic acid being the template of nucleic acid serves to synthesize a multitude of nucleic acids which are then detected with the method of the invention.

When detecting bacteria, for example in foods, the method of the invention could also be preceded by several steps.

Generally, bacterial samples are digested, if necessary after in-vivo replication of the bacteria under conditions which allow lysis of the bacterial cell walls (e.g. proteinases, alkali). In the case of samples with very low concentrations, this may also be followed by in-vitro amplification of the analyte-nucleic acid of the bacterium.

These various pretreatments always produce a sample liquid which contains the nucleic acids in a dissolved state and, if preparatory steps were necessary, also the reagents and the lysed cell components.

The method of the invention now proposes the treatment of the sample under alkaline conditions, where at least one detergent from the group of the anionic, non-ionic and zwitterionic detergents is present. The conditions are such that the nucleic acids present in the liquid are converted into single-stranded nucleic acids provided this is not already the case. To do this, an alkali hydroxide, preferably sodium hydroxide, is added to the liquid in the form of solid substance or, preferably, as a solution (denaturing solution) in an amount which, after addition, produces a sample pH ranging between 9.5 and 14, preferably between 11 and 13.5. The solution added may also contain further additives (e.g. salts and buffer).

Gist of the invention is the finding that the presence of certain detergents during treatment under alkaline conditions for conversion into single strands brings about significant advantages. When implementing the invention, this detergent is added to the sample liquid either as a solid substance or, preferably, in the form of a solution such that the concentration of the detergent in the sample liquid amounts to 0.01 wt. % to 10 wt. %, preferably 0.05 wt. % to 5 wt. %. It is possible to add the detergent to the prepared sample liquid either prior to or after adjusting to alkaline conditions. In a particularly preferred manner, the detergent, when added to the sample liquid, is either already contained in the alkaline denaturing solution or added together with the latter. The detergent concentration in the denaturing solution is preferably between 0.01 and 15 wt. %, the particularly preferred concentration ranging between 0.05 to 10 wt. %.

Preferred non-ionic detergents include polymers of poly-($C_2$–$C_6$)-alkoxy-($C_2$–$C_6$)-alkylenes, esters and ethers of poly-($C_2$–$C_6$)-alkyleneglycols and glycosides of $C_6$–$C_{20}$ alkylalcohols. Specifically preferred non-ionic detergents include Synperonic (block copolymer made from poloxyethylene and polyethoxypropylene, Pharmacia), Tween 20 (polyethylene glycol (20) sorbitan monolaurate), Thesit® (dodecylpolyethylene glycol ether), NP-40 (ethylenephenolpolyethyleneglycolether), TritonX-100 (polyethylene glycol (9-10) p-t-oktylphenol) and glycosidic detergents, e.g. octyl:β-D-glucopyranoside.

Particularly effective in terms of the invention are Synperonic and NP-40.

Preferred anionic detergents include sulfates of $C_6$–$C_{20}$ alkylalcohols and N-$C_6$–$C_{20}$-acylaminoacids. Examples of anionic detergents include SDS (sodium dodecyl sulfate), sodium lauryl sarcosin and sodium deoxycholate. The preferred substance from this group is SDS.

Preferred Zwitterionic detergents are N-$C_1$–$C_{16}$-alkyl-ammonio-$C_2$–$C_6$-alkyl-sulfonates. Examples of Zwitterionic detergents include Zwittergent 3-08 (N-octyl-N,N-dimethyl-3-amino-1-propane sulfonate) Zwittergent 3-12 (N-docecanyl-N,N-dimethyl-3-ammonio-1-propane sulfonate), CHAPS (3-[(3-cholamidopropyl)-dimethyl-ammonio]-1-propane sulfonate) and CHAPSO (3-cholamidopropyl)-dimethylamino]-2-hydroxy-1-propane sulfonate). Zwittergent 3-12 proved to be particularly effective.

In accordance with the present invention, the conditions for conversion into single strands can be maintained for a period from 1 min to 8 hours without producing any noticeable decomposition of the nucleic acids to be detected. In a preferred manner, more than 90% of the originally present nucleic acids are still detectable after 4 hours.

Denaturing is preferably allowed to occur in a plastic vessel. This includes in particular those vessels which are used in conventional automated analyzers as sample storage containers. Examples include containers made of polystyrene, polyethylene or luran. During treatment with alkali and detergent, the vessel in which the treatment is allowed to occur, is preferably already in an analyzer, particularly preferred on a sample rotor allowing a sampling device to access individual sample containers placed on the rotor.

The invention is particularly useful when used in connection with analyzers and analysis procedures where the standing times of the filled sample storage containers vary from container to container leading, hence, to periods of alkali treatment of different lengths (i.e. irregular intervals). It is an advantage of these automated analyzers that in case of an emergency, analysis of certain samples can be carried out first leaving the analysis of other samples for a later time.

Another essential step in the method of the invention is the addition of an immobilizable or immobilized capture probe. This can be done by adding a solution of an immobilizable capture probe to the solution with a single-stranded nucleic acid using a pipette, for example, or by bringing it into contact with a solid substance to which a capture probe is bound.

An immobilizable capture probe is understood to be a nucleic acid whose structure differs from a normal nucleic acid which is essentially complementary to the nucleic acids to be detected in that it has one of several groups I capable of immobilization. In a preferred case, the capture probe is a single-stranded nucleic acid probe without the complementary strand being added. The solution with a single-stranded capture probe also preferably contains hybridization-promoting reagents such as SSC, formamide (if longer fragments are present) or blocking reagents for nucleic acids that are not to be detected as well as preferred reagents for the correct adjustments of the pH value. A particularly preferred capture probe is a nucleic acid as described in DE-A-41 23 540 (corresponding to U.S. patent application Ser. No. 07/914,285, abandoned Dec. 16, 1993).

The immobilizable nucleic acid probe according to DE-A-41-23 540 contains two or more nucleotides modified by immobilizable groups which are not directly adjacent in the nucleotide sequence. Apart from the number of ligands (reporter groups) the distance between the ligands is crucial and should be preferably 10 or more nucleotides in order to observe this effect. For example oligodeoxyribonucleotide probes which contained 5 biotin residues (biotin corresponds to the ligand) coupled in direct succession and were used as capture probes to bind an analyte to a streptavidin matrix did not result in an increase in the sensitivity in the total assay compared to a reference probe which was only linked to one biotin residue. The "capture probe" can be an oligonucleotide or a polynucleotide (DNA or RNA) which can hybridize in a suitable manner with the analyte nucleic acid to be detected. It can be single-stranded (e.g. oligodeoxyribonucleotido, oligoribonucleotide) or double-stranded (e.g. plasmid, fragment). In the latter case the capture probe has to be denatured before hybridization with the analyte. A particularly preferred embodiment utilizes nucleic acid probes in which the terminal nucleotides of the nucleic acid probe are modified in each case.

An oligodeoxynucleotide is preferred which has a length between 11 and 40 nucleotides whereby the label is appropriately attached to the 3' and 5' end in order to meet the requirement for distance as described above.

Single-stranded capture probes can, for example, be obtained through chemical nucleic acid synthesis according to DE-A-39 16 871 or according to EP-B-0 184 056 (corresponding to U.S. Pat. No. 4,734,363).

When practicing the method of detection on an automated analyzer, the hybridization solution is in a preferred manner automatically taken from a reagent storage container which is placed on a rotor holding reagents for several different determinations. Said hybridization solution is then combined with an aliquot of the liquid containing the denatured nucleic acids to be detected. In a particularly preferred manner, the analyzer first removes a given volume from a sample storage container and then a given volume of hybridization solution from a given reagent storage container, both volumes being then poured into an immobilization and detection container.

Groups I which are capable of immobilization, are chemical groups, for example, which are normally not present in naturally occurring nucleic acids and can be bound to a solid phase in chemical reaction or a photo-reaction. Groups I may also be groups or parts of molecules which are recognized by another molecule or parts of a molecule through group-specific interactions and can thus be bound. Such groups include, for example, haptens, antigens and antibodies, nucleotide sequences, receptors, regulation sequences, glycoproteins, for example lectins, or even the binding partner of binding proteins, such as biotin or iminobiotin. Preferred groups are vitamins and haptens, particularly preferred are biotin, fluorescein or steroids, such as digoxigenin or digoxin.

During incubation of the capture probe with the single-stranded nucleic acid to be detected the latter two hybridize to form a hybrid D. If additional nucleic acids, e.g. detection probes, are to be hybridized with single-stranded parts, of a hybrid D, they can already be added to this mixture and can be allowed to hybridize, as desired.

The liquid, which contains the nucleic acid hybrid D in a dissolved form if the nucleic acid to be detected was present in the sample, is brought in contact with the solid phase acid capable of specifically binding the hybrid D via the immobilizable groups of the nucleic acid probe. The type of solid phase is detected by group I capable of immobilization. The latter preferably has an immobilizing group R capable of providing a binding interaction with I. If, for example, the immobilizable group is a hapten then a solid phase can be used whose surface has an antibody to this hapten. If the immobilizable group is a vitamin. e.g. biotin, then the solid phase can contain binding proteins such as avidin or streptavidin in an immobilized form. Particularly preferred residues I and R are biotin and streptavidin. Immobilization via a group at the modified nucleic acid is particularly advantageous since it can occur under milder conditions than, for example, hybridization reactions.

In a preferred manner the reaction mixture in order to immobilize the synthesized nucleic acids, is filled into a vessel prior to or during or after synthesis of the nucleic acid hybrid D. The reaction with the immobilizable group can occur at the surface of this vessel. In a preferred manner, the hybridization reaction with a probe occurs essentially at the same time as the immobilization. It is possible to use a solid phase in the form of a porous material, such as a membrane, a fabric, or a fleece, onto which the reaction mixture can be applied. It is also possible to use beads or latex particles. Preferred vessels include cuvettes, tubes or microtiter plates. The solid phase should have at least as many binding sites for the immobilizable group of the probe as there are nucleic acid hybrids D and, hence, nucleic acids to be detected.

Reference is made in full to EP-A-0 344 578 which describes the preparation of a preferred solid phase.

In a particularly preferred embodiment which can be run on an automated analyzer, the solution with the denatured nucleic acid of the invention is poured into a vessel which contains at its surface in a bound form a specific binding partner for an immobilizing group of the capture probe. The hybridizing solution containing a single-stranded capture probe which has an immobilizing group is also added into the vessel. This neutralizes the reaction mixture. Any nucleic acid to be detected which has hybridized with the capture probe is bound to the solid phase.

An immobilized capture probe is understood to be a nucleic acid which is essentially complementary to at least a part of the nucleic acid to be detected. Said essentially complementary nucleic acid is already bound to a solid phase at the time of addition. The binding can be covalent, but may also be based on biospecific interactions as described in connection with immobilizable probes. The solid phase can be a vessel, but also a solid substance of another geometry, e.g. a sphere which requires another vessel.

After a period of incubation during which the immobilization reaction to occur, the liquid phase is removed from either the container, the porous material or the pelleted beads. Subsequently, the solid phase can be washed with a suitable buffer since the binding of the hybrid D to the solid phase is very efficient.

The amount of hybrid consisting of nucleic acid to be detected and capture probe which is bound to the solid phase can be determined in a principally known manner. On the one hand this can be done with the aid of a capture probe according to the sandwich hybridization method. In this method the hybrid is reacted with a detection probe which is complementary to a nucleotide sequence of the nucleic acid to be detected which is different from the sequence to which the capture probe is specific and is hybridized with it. The result formed at the solid phase is a hybrid consisting of detection probe, nucleic acids to be detected and capture probe. Such a method is, for example, described in EP-A-0 079 139. In a preferred manner, the detection probe is added to the hybridization solution together with the capture probe.

In the event that the method of detection according to the invention is preceded by an amplification reaction, it is preferable to incorporate a detectable group into the replication product (which is the nucleic acid to be detected) during the amplification reaction. Such a method is, for example, described in DE-A-4 041 608. In the method described in that publication, a mononucleoside triphosphate is incorporated into the amplification reaction. In this case, hybridization with a detection probe is no longer necessary since the label of the nucleic acid to be detected can be detected.

In directly detectable groups, for example fluorescent labels, the amount of labelling is fluorometrically determined. If the detectable group can be indirectly detected. e.g. a hapten, the modified nucleic acid is preferably reacted with a labelled antibody to this hapten as is described correspondingly in EP-A-0-324 474. The labelling at the antibody can, for example, be a color or fluorescent label or, preferably, an enzyme label, such as $\beta$-galactosidase, alkaline phosphatase or peroxidase. If an enzyme label is used, the amount of nucleic acid is measured in a photometric, chemoluminometric or fluorometric monitoring of the enzyme reaction with a chromogenic, chemoluminogenic or fluorogenic substrate. The resulting signal is a measure for the amount of originally present nucleic acid to be detected and, hence, organisms to be detected.

In a preferred manner, the hybrid synthesized is detected with the aid of an automated analyzer. To do this, the sample liquid is separated from the immobilized hybrids after incubation of the single-stranded nucleic acid with the capture probe and, if used, the detection probe. This can be done, for example, by removing the liquid from the immobilized hybrids. This depends on the kind of solid phase. If, for example, a vessel is used, the liquid is removed from this vessel by means of pipetting, for example. Following one or several washing steps to completely remove non-immobilized capture probe and, if necessary, detection probe and detectably labelled mononucleoside triphosphate, a measurement (direct labelling) is carried out or an enzyme substrate is added and the released cleavage product (enzyme labelling) is measured. In a preferred manner, the vessel used for the hybridization reaction is also used for the measurement.

From the above it can be understood that the method of the invention can be applied without intermediate separation of the nucleic acids to be detected beginning with the step where the analyte nucleic acid is present in the prepared sample solution in a dissolved state until the step where the immobilized hybrid consisting of nucleic acids to be detected and capture probe is present. This brings about a considerable handling advantage. Moreover, the method has the advantage of running on automated analyzers as they are generally known for immunoassays (see for example EP-A-098 590, U.S. Ser. No. 08/077,500, issued as U.S. Pat. No. 5,501,984, which is a continuation of U.S. Ser. No. 07/874, 996 which is a continuation of U.S. Ser. No. 07/551,827). This allows simultaneous processing of immunological parameters as well as parameters from the field of nucleic acid diagnosis. Further, the method of the invention has the advantage of being very accurate. As compared to methods that are run without the addition of certain detergents, great deviations are found among the results of different measurements of the same sample whereas in the method of the invention, deviations are less than 5%. This, however, is a prerequisite for the reliable quantitative automated detection of nucleic acids. It was in particular the fact that the standing times of sample vessels vary greatly when automated analyzers are used which prevented quantitative nucleic acid hybridization tests from being run on analyzers for immunological tests.

Another subject matter of the invention is a reagent kit for immobilizing a nucleic acid. Said reagent kit contains in separate containers a capture probe which is specific to a nucleic acid to be immobilized and a reagent containing an alkali hydroxide and at least one detergent from the group of the anionic, non-ionic and zwitterionic detergents. Further, the reagent kits can contain components which promote immobilization of nucleic acids, for example, a plastic vessel at which the nucleic acid can be immobilized with the aid of the capture probe.

Again another subject matter of the invention is a reagent kit for the detection of nucleic acids which contains the components of the reagent kit for immobilizing a nucleic acid and at least one additional nucleic acid which, preferably, is specific to the nucleic acid to be immobilized at a sequence that is different from the one of the capture probe. Preferably, this additional nucleic acid carries a detectable label and acts as a detection probe.

Yet another subject matter of the invention is an analysis system for the automated determination of diagnostic parameters in sample solutions. Said system comprises at least one sample storage container in a sample rotor, at least one reagent storage container on a reagent rotor, the latter containing a denaturing solution for nucleic acids under alkaline conditions with at least one detergent from the group of anionic, non-ionic and zwitterionic detergents, and at least one reagent storage container containing an immobilizable or immobilized parameter-specific capture probe. Further, this analysis system contains a device for the automated processing of nucleic acids to be detected while having access to the probe, a denaturing solution and the capture probe.

Diagnostic parameter refers to an analyte containing a nucleic acid (for example a bacterium or virus) or refers to a state of an organism which is linked with a specific nucleic acid sequence (for example an illness caused by a mutation of nucleobases on a nucleic acid). Thus, the analysis of a diagnostic parameter includes the determination of a nucleic acid.

Yet another subject matter of the invention is the use of glycosidic detergents in methods of detecting nucleic acids. Glycosidic detergents are understood to be compounds which contain sugar residues and reduce the surface tension of liquids.

Figure 1:
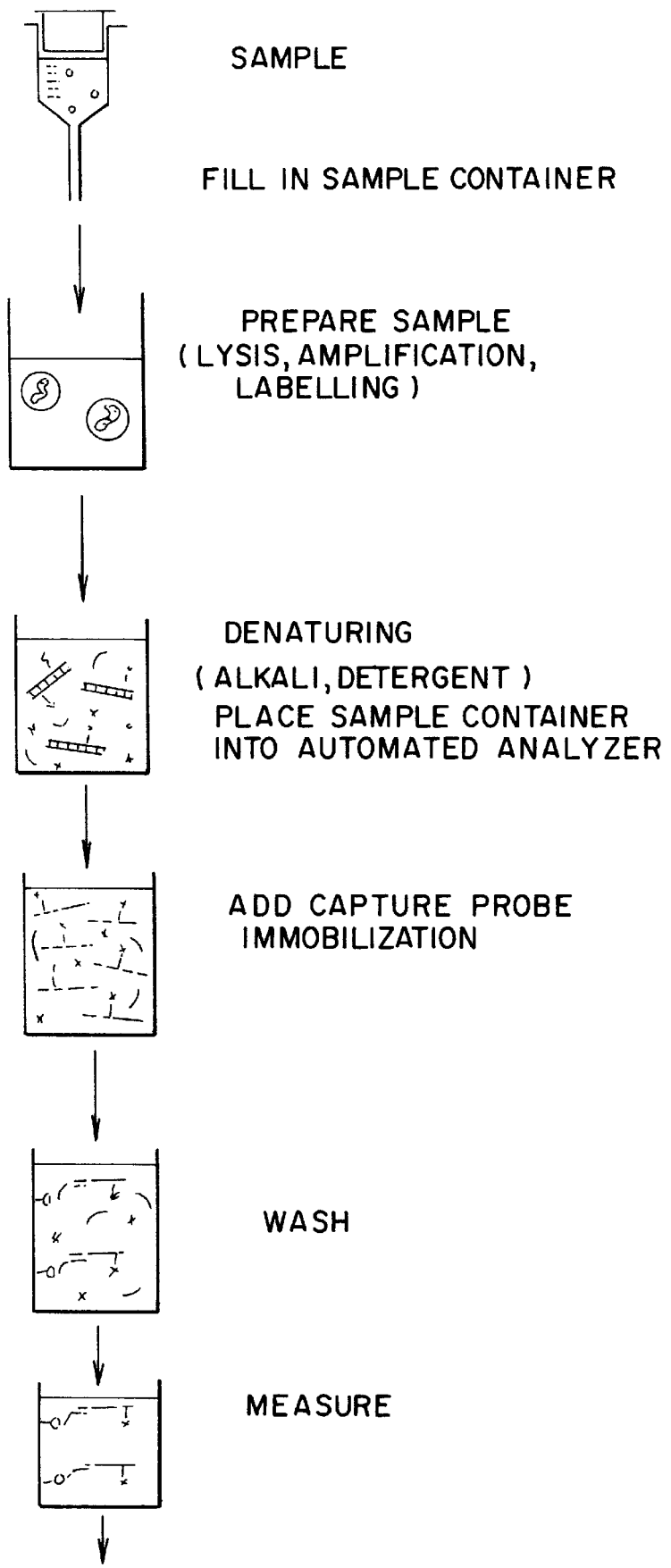
FIG. 1 is a diagrammatic representation of a particularly preferred embodiment of the method of the invention.

The following examples explain the invention in greater detail.

EXAMPLE 1
Digestion of HBV-DNA-containing Sera (Lysis)

10 μl HBV-containing serum are mixed with 10 μl 0.2 N NaOH and incubated for 1 h at 37° C. Subsequently, 30 μl neutralization solution (100 mM KCl, 20 mM Tris/HCl, 3 mM $MgCl_2$, 0.67 N HCl) are added.

One aliquot of this mixture is used in the PCR amplification.

EXAMPLE 2
PCR amplification and Labelling of HBV-DNA with Digoxigenin

20 μl of sera as digested in example 1 are used in the PCR amplification according to the following table:

| Reagent or sample | Concentration of solution prepared | Final concentration in PCR |
|---|---|---|
| sample | | 20 μl/100 μl mixture |
| primer 1 | 5 μM | 200 nM |
| primer 2 | 5 μM | 200 nM |
| dATP (Na-salt) | 4 mM | 200 μM |
| dCTP (Na-salt) | 4 mM | 200 μM |
| dGTP (Na-salt) | 4 mM | 200 μM |
| dTTP (Na-salt) | 4 mM | 175 μM |
| Dig-11-dUTP | 1 mM | 25 μM |
| PCR buffer | 10 x | 1 x |
| Taq-polymerase | 5 U/μl | 2.5 U |

10×PCR buffer: 100 mM Tris/HCl. 500 mM KCl, 15 mM $MgCl_2$, 1 mg/ml gelatine, pH 9.0.

Dig-11-dUTP: Digoxigenin-11-dUTP, Li-salt (Boehringer Mannheim)

Primer 1: oligonucleotide of HBV sequence 2269–2289

Primer 2: oligonucleotide of HBV sequence 2419–2439, reverse

The PCR batches are amplified in a Perkin Elmer Thermal Cycler with 30 cycles of 30 sec at 92° C., 30 sec at 50° C. and 1 min at 70° C.

EXAMPLE 3
PCR Amplification and Labelling of HBV-DNA with $\alpha^{-32}P$ dCTP Principally, amplification and labelling are carried out as in example 2. dCTP is replaced by 5 μl of $\alpha^{-32}P$ dCTP (10 μCi/μl. 1000 nCi/nmol). The final concentration of dTTP is 200 μM and no Dig-11-dUTP is used.

EXAMPLE 4
Denaturing and Detection of Amplified DNA

A polystyrene or polyethylene container is used to dilute digoxigenin-labelled DNA from an amplification reaction (PCR [H. A. Ehrlich ed. 1989 PCR technology: Principles and applications for DNA amplification, Stockton Press, New York], LCR (Biotechnica, EP-A-0320308), RCR (Segev Diagnostics, [WO 90/01069] or the system known from WO 91/03573) 1:10 with denaturing solution (0.05 N NaOH, 0.9 NaCl, 0.1% Na-laurylsarcosin, pH 12.5). The standing time can vary between 0 and 8 hours (temperature: 5° C.–45° C.). On an ES 300® analyzer (Boehringer Mannheim), 100 μl of this mixture are incubated in a TBSA streptavidin-coated tube (EP-A-0344578) for 3 hours at 37°

C. with 400 μl hybridization buffer which contains a biotinylated (EP-A-0063879) capture probe. The hybridization buffer contains 62.5 mM Na-phosphate buffer, 0.94 M NaCl, 94 mM Na-citrate, 0.125% Na-laurylsarcosin, 0.6% bovine serum albumin, pH 6.5. The biotinylated capture probe is present in the hybridization buffer at a concentration ranging between 25 and 150 ng/ml. For amplified HBV-DNA as described in example 2, a biotinylated capture probe of the $HBV_{adw}$-sequence 2332–2351 with 50 ng/ml is used. Incubation is followed by washing 3×with Enzymun® wash solution. Then, 500 μl conjugate solution (50 mU/ml anti-digoxigenin-POD-conjugate (Boehringer Mannheim) in 100 mM Tris/HCl. pH 7.5, 0.9% NaCl, 0.5% bovine serum albumin) are added with a pipette. After incubation for 30 min at 37° C., the mixture is washed again with Enzymun® wash solution and then incubation is continued for another 30 min with substrate (ABTS® Boehringer Mannheim). Then, absorbance is measured at 422 nm.

Figure 2:
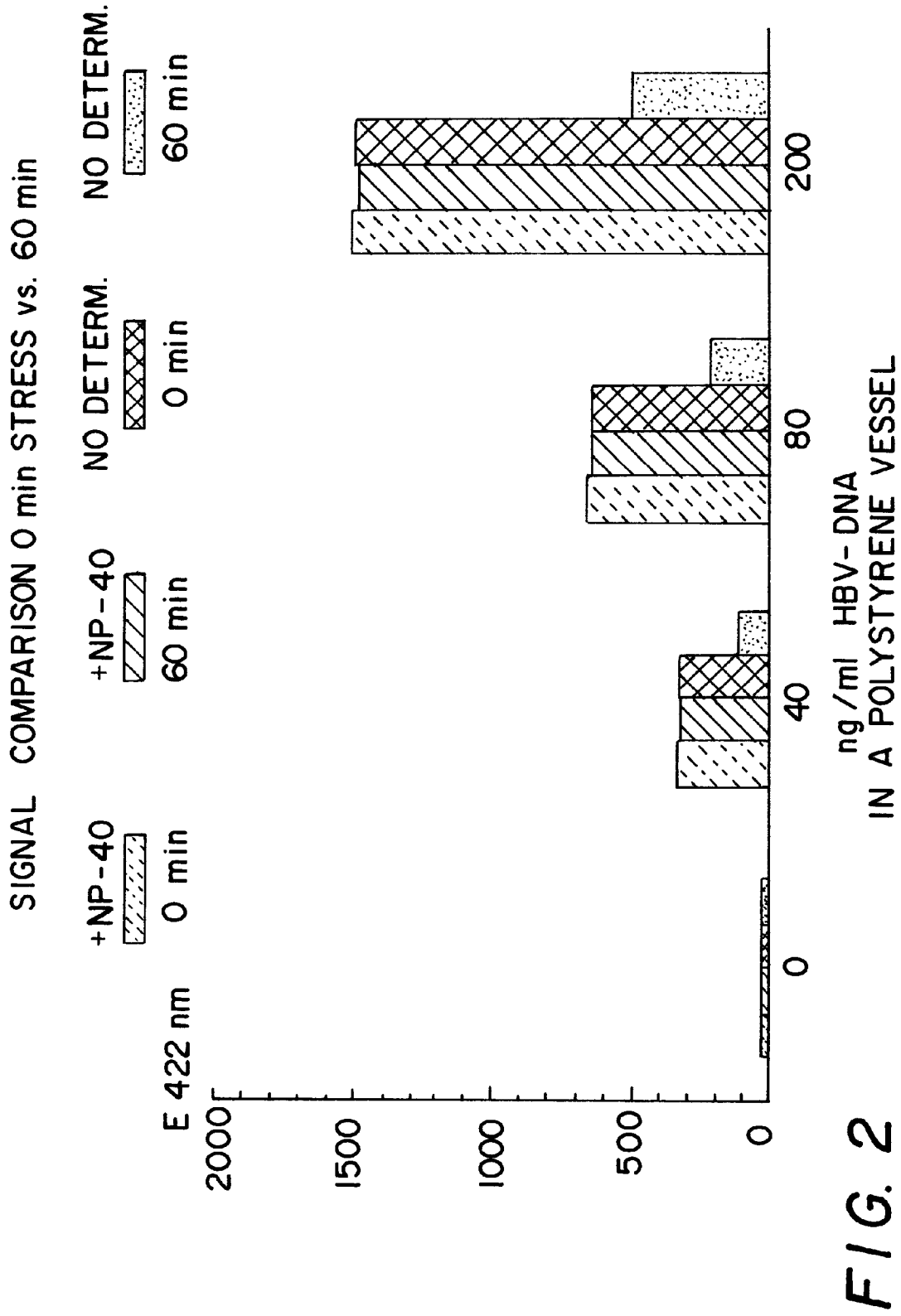
FIG. 2 is a graph representing the stability of DNA under alkaline conditions (absorbance at 420 mm). From the graph it can be understood that, if NP-40 is used the absorbance of DNA and, hence, its stability is almost the same after 60 minutes as it was at the beginning of the experiment. Without any detergent added, the amount of DNA after 60 minutes has decreased by more than half. This applies to all three concentrations of HBV-DNA. (40, 80, 200 ng HBV-DNA/ml).

EXAMPLE 5
Denaturing and Detection of Non-amplified DNA 10 to 200 ng cloned HBV-DNA (nucleotide 29-2606 of the $HBV_{adw}$-sequence cloned in pUCBM20) are denatured in a polystyrene vessel using 0.1 N NaOH, 0.9 NaCl, 0.1% NP-40, pH 13. To have a comparison, the assay is prepared again with the same denaturing solution, however, without NP-40. After incubation for 60 min, the denatured DNA is incubated for 3 h with 500 μl hybridization solution. Then it is washed 3×with Enzymun® wash solution and conjugate solution (cf. example 4) is added with a pipette, incubated for 60 min at 37° C., washed again and after the substrate reaction (60 min) with ABTS®, absorbance is measured at 422 nm. The results are compiled in FIG. 2.

Hybridization solution: portions of 200 ng/ml biotinylated (HBV-sequence 2456–2417 and digoxigenin-labelled (HBV-sequence 287–246) oligonucleotide probe in 62.5 mM sodium phosphate buffer, 0.9 M NaCl, 90 mM Na-citrate, 0.1% bovine serum albumin, 0.125% Na-laurylsarcosin, pH 6.5.

Labelling with digoxigenin was carried out with a terminal transferase (K. Mühlegger, E. Huber, H. von der Eltz, R. Rüger & C. Kessler 1990 Biological Chemistry Hoppe-Seyler 371, 953–65).

EXAMPLE 6

Comparison of different classes of detergents for DNA-stabilization under alkaline conditions.

The detergent concentration was 0.1%. The vessels used were made of polystyrene. All other reaction conditions are given in examples 1–4.

| Detergent | NaOH mol/l | % Signal after 240 min | CV (0 min) | CV (240 min) |
|---|---|---|---|---|
| None | 0.1 | 26.3 | 11.9 | 12.1 |
| None | 0.05 | 36.5 | 4.5 | 19.5 |
| Non-ionic | | | | |
| Synperonic | 0.05 | 98.7 | 1.2 | 0.8 |
| Tween 20 | 0.05 | 95 | 1.4 | 3.0 |
| Thesit | 0.05 | 92.7 | 1.9 | 1.3 |
| Triton X-100 | 0.05 | 95.1 | 1.2 | 1.1 |
| NP-40 | 0.05 | 99 | 0.8 | 0.8 |
| Octyl gluco-pyranoside | 0.05 | 91.7 | 0.9 | 1.3 |
| Anionic | | | | |
| SDS (sodium lauryl sulfate) | 0.05 | 99 | 0.6 | 0.8 |
| Sodium lauryl sarcosin | 0.1 | 93 | 2.9 | 1.9 |
| Sodium deoxycholate | 0.05 | 90.1 | 1.1 | 2.3 |
| Zwitterionic | | | | |
| Zwittergent 3-08 | 0.05 | 93.5 | 1.9 | 3.4 |
| Zwittergent 3-12 | 0.05 | 98.9 | 0.8 | 0.9 |
| Chaps | 0.1 | 93.4 | 2.2 | 2.5 |
| Chapso | 0.1 | 92.8 | 2.2 | 3.2 |
| Kationic | | | | |
| Cetyltrimethyl ammonium bromide | 0.05 | 67 | 1.4 | 2.5 |

CV = coefficient of variation (20 samples)

EXAMPLE 7

The effects of different stabilizing reagents in different plastic containers

| Plastic | Pre-treatment | Substance added | % Signal after 240 min | CV (0 min) | CV (240 min) |
|---|---|---|---|---|---|
| PS | None | None | 36.5 | 4.5 | 19.5 |
| PS | Siliconized | None | 68.0 | 4.4 | 12.3 |
| PS | None | 0.5% bovine IgG | 55.0 | 6.8 | 10.3 |
| PS | None | 100 μg/ml calf-thymus DNA | 76.0 | 1.4 | 7.3 |
| PS | None | 50 μg/ml calf-thymus DNA | 56.8 | 3.5 | 7.7 |
| PS | None | 100 μg/ml herring sperm DNA | 85.4 | 1.9 | 7.8 |
| PS | None | 100 μg/ml poly-A DNA | 66.0 | 3.3 | 23.1 |
| PS | None | 0.1% sodium lauryl sarcosin | 95.0 | 2.2 | 1.1 |
| PE | None | None | 74.4 | 5.1 | 7.7 |
| PE | Siliconized | None | 86.4 | 2.2 | 5.4 |
| PE | None | 0.1% sodium lauryl sarcosin | 96.3 | 2.0 | 1.1 |
| Luran | None | None | 70.6 | 5.7 | 8.5 |
| Luran | None | 0.1% sodium lauryl sarcosin | 94.2 | 2.3 | 1.9 |

PS = Polystyrene; PE = Polyethylene; Luran = Copolymer made of polystyrene and acrylonitrile.
The reaction conditions are the same as in examples 1 to 4.

We claim:

1. A method for the detection of nucleic acids in different samples, comprising the steps of
   a) amplifying nucleic acids in any samples to be tested,
   b) adding at least one detergent selected from the group consisting of anionic, non-ionic and zwitterionic detergents to said amplified nucleic acids under alkaline conditions to form reaction mixtures, said detergents being present in a stabilizing amount between 0.01 wt % and 10 wt %, wherein said alkaline conditions are at a pH between 10 and 14,
   c) incubating said reaction mixtures in plastic vessels at least until any double stranded nucleic acids present in the reaction mixtures are converted into single stranded nucleic acids,
   d) adding immobilizable or immobilized capture probes to said reaction mixtures,
   e) hybridizing said single stranded nucleic acids with said capture probes to form immobilized hybrids, and
   f) determining the amount of immobilized hybrids.

2. The method according to claim 1, wherein said immobilized hybrids are determined using detectably labeled probes or via a detectable label which has been incorporated into said amplified nucleic acids.

3. The method according to claim 1, wherein said plastic vessels are made of polystyrene.

4. The method according to claim 1, wherein the incubation time in step c) is different for each reaction mixture.

5. The method according to claim 1, wherein the detergent is present during steps c), d) and e).

6. The method according to claim 1, wherein said non-ionic detergents are selected from the group consisting of polymers of poly-$(C_2-C_6)$-alkoxy-$(C_2-C_6)$-alkylenes, esters and ethers of poly-$(C_2-C_6)$-alkyleneglycols and glycosides of $C_6-C_{20}$ alkylalcohols.

7. The method according to claim 1, wherein the immobilized capture probe is added to the reaction mixture in the form of a solution having a pH of less than 7.5, wherein said solution neutralizes the alkaline conditions in step b).

8. The method according to claim 1, wherein steps a)–e) are carried out with an automated analyzer.

9. A method of stabilizing amplified single-stranded nucleic acids in an alkaline solution by adding 0.01 wt %–10 wt % of a detergent selected from the group consisting of an anionic, non-ionic or zwitterionic detergent to said nucleic acids in solution, wherein said alkaline solution has a pH between 10 and 14.

10. A method for storing individual nucleic acid samples in alkaline solutions in an analyzer, wherein analysis of said individual nucleic acid samples can be carried out at different times, comprising adding an alkaline solution of a detergent selected from the group consisting of non-ionic and zwitterionic detergents to said nucleic acid samples, wherein said alkaline solution is at a pH between 10 and 14, and wherein said detergent is present in an amount between 0.01 wt %–10wt %.

11. A reagent kit for immobilizing a nucleic acid comprising the following components in separate containers:
   a) a capture probe specific for the nucleic acid to be immobilized, wherein said capture probe is in a solution which has a pH of less than 7.5,
   b) a reagent containing an alkali hydroxide and at least one detergent selected from the group consisting of anionic, non-ionic and zwitterionic detergents, wherein said alkaline conditions are at a pH between 10 and 14 and wherein said detergent is present in an amount between 0.01 wt %–10wt %, and
   c) a plastic vessel made of polystyrene.

12. A reagent kit for detecting a nucleic acid, comprising:
   a) a capture probe specific for the nucleic acid to be detected, wherein said capture probe is in a solution which has a pH of less than 7.5,
   b) a reagent containing an alkali hydroxide and at least one detergent selected from the group consisting of anionic, non-ionic and zwitterionic detergents, wherein said reagent is at a pH between 10 and 14, and wherein said detergent is present in an amount between 0.01 wt %–10 wt %,
   c) at least one additional nucleic acid which is specific for the nucleic acid to be detected, and
   d) a plastic vessel made of polystyrene.

13. A reagent kit according to claim 12, wherein said at least one additional nucleic acid is detectably labeled.

14. A method of detecting a nucleic acid comprising the steps of:
   a) converting a nucleic acid into a single-stranded nucleic acid under alkaline conditions in the presence of a stabilizing amount of a glycosidic detergent, wherein said detergent is present in an amount between 0.01 wt %–10 wt % and said alkaline conditions are of a pH between 10 and 14,
   b) adding an immobilizable or immobilized capture probe,
   c) immobilizing the nucleic acid via said capture probe by hybridizing said capture probe with the nucleic acid to form an immobilized hybrid, and
   d) detecting the amount of immobilized hybrid.

15. method for stabilizing single-stranded nucleic acids in an alkaline solution by adding a glycosidic detergent to said solution, wherein said detergent is present in an amount between 0.01 wt %–10 wt % and said alkaline conditions are at a pH between 10 and 14.

* * * * *